United States Patent [19]
Bowen

[11] Patent Number: 5,804,264
[45] Date of Patent: Sep. 8, 1998

[54] MEMBRANE PERMEABLE TO FRANGRANCES AND OTHER PRODUCTS

[75] Inventor: William Edmund Bowen, Neenah Winnebago, Wis.

[73] Assignee: American National Can Company, Chicago, Ill.

[21] Appl. No.: 475,699

[22] Filed: Jun. 7, 1995

[51] Int. Cl.[6] .............................. A61L 9/12; B32B 27/32; B65D 17/00

[52] U.S. Cl. ................... 428/35.2; 156/243; 156/244.25; 156/246; 239/6; 239/43; 264/173.19; 264/213; 428/35.7; 428/41.8; 428/212; 428/515; 428/516; 428/905

[58] Field of Search ...................................... 428/515, 516, 428/905, 35.2, 212, 35.7, 41.8; 239/43, 6, 34, 52, 54, 53, 55; 264/173.19, 213; 156/243, 244.27, 246, 289, 323

[56] References Cited

U.S. PATENT DOCUMENTS

| | | | |
|---|---|---|---|
| 4,145,011 | 3/1979 | Weyenberg et al. | 239/56 |
| 4,849,606 | 7/1989 | Martens, III et al. | 219/271 |
| 4,886,690 | 12/1989 | Davis et al. | 428/36.6 |
| 5,491,019 | 2/1996 | Kuo | 428/213 |

*Primary Examiner*—Paul J. Thibodeau
*Assistant Examiner*—D. Lawrence Tarazano
*Attorney, Agent, or Firm*—McDermott, Will & Emery

[57] ABSTRACT

A multilayer permeable membrane with a release layer for the packaging of aromatic condensation products. The permeable membrane has a first layer comprising low density polyethylene, a second layer comprising ultra low density polyethylene and a third layer comprising low density polyethylene. The release layer is adhered to the first layer and may be peeled away from the permeable membrane to expose the membrane and provide for the controlled release of vapors over a period of time.

6 Claims, 2 Drawing Sheets

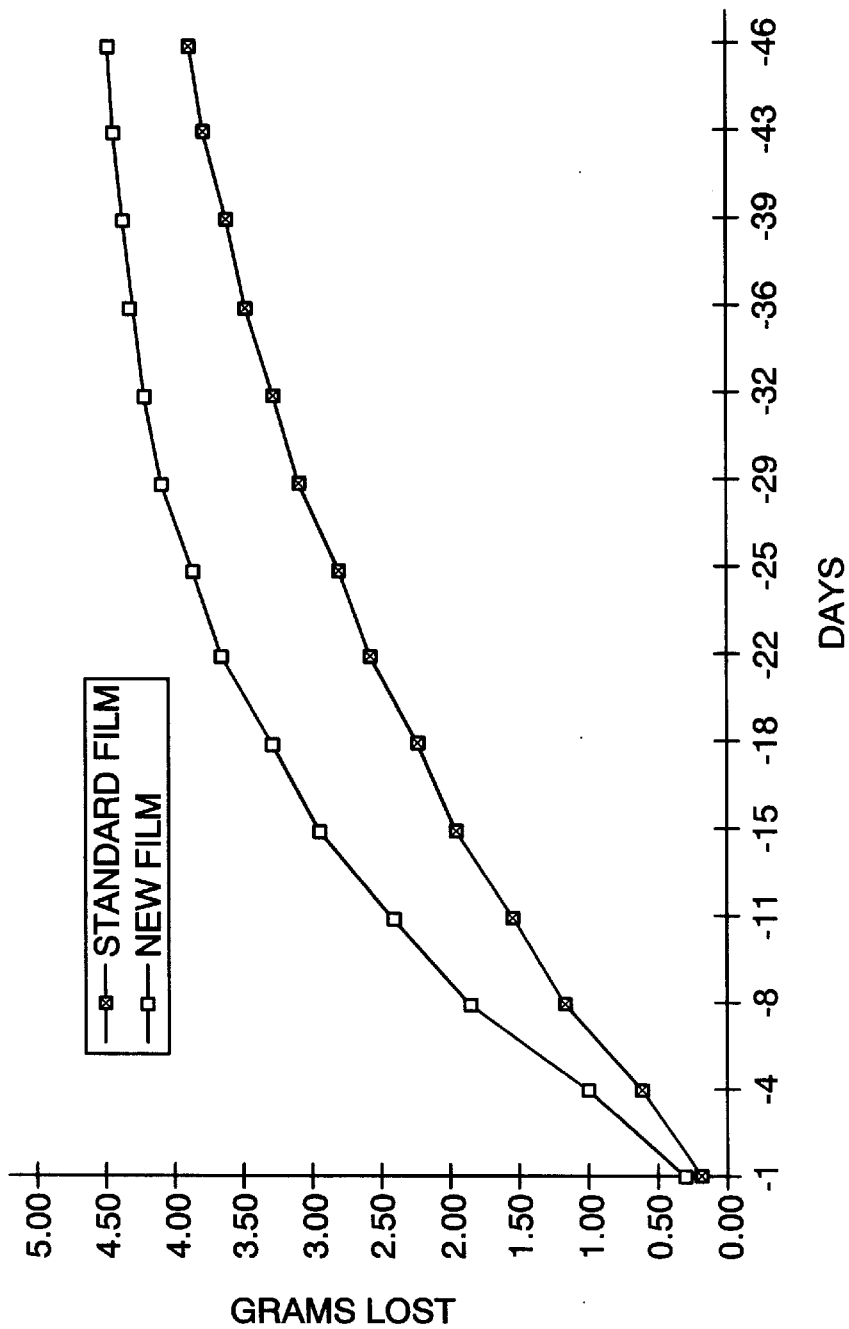

MEMBRANE PERMEABLE TO FRANGRANCES AND OTHER PRODUCTS

BACKGROUND

1. Field of the Invention

This invention pertains generally to the field of permeable membranes and packaging for volatile materials, such as fragrances and other aromatic products, and more particularly, to membranes and packages which allow the controlled release of vapors over a period of time.

2. Description of the Art

The controlled time release of very volatile substances, such as fragrances and other aromatic products, presents a number of packaging problems. Room "air fresheners" or fragrances have usually been packaged in glass bottles or vials, with the fragrance being released into the atmosphere by transmission through an absorbant wick, which is capped until the time of use. However, glass bottles are bulky and breakable, and generally it is not economical to package fragrances in small quantities inside glass containers because of the cost of the container itself.

Many other common packaging materials, including some plastic films, are permeated by the fragrance before the desired release, or are subject to attack by the fragrance itself or by its liquid carrier.

One proposed alternative method of packaging room fragrances, is to place a breakable glass vial within a plastic container formed of a material which is permeable to the vapors of the volatile fragrance. The user deliberately breaks the glass vial to allow the fragrance liquid to seep into the absorbant pad, and the vapors from the liquid slowly diffuse into the atmosphere through the permeable outer container. Such containers may be subject to accidental breakage of the glass vial during shipping and handling as well as possible puncture of the container by broken glass, while the presence of the glass vial increases the manufacturing costs of such a container.

Other fragrance dispensers utilize sealed packages which are opened by peeling back a covering foil to expose a perforated panel covering an absorbant pad filled with the fragrance liquid. The costs of such containers makes them generally inappropriate for dispensing small amounts of the fragrance. It is also somewhat difficult to obtain controlled release of the fragrance at a fairly constant rate over the life of the product because of the direct exposure of the liquid with the atmosphere.

U.S. Pat. No. 4,145,001 issued to Weyenberg et al., discloses a dispenser having a permeable membrane. The dispenser is opened by peeling back a covering foil to expose the membrane. However, the membrane disclosed has limited permeation for certain fragrances.

For the foregoing reasons, there is a need for a permeable membrane which provides controlled release and increased permeation for a broad range of fragrances.

SUMMARY

This invention relates to an improved permeable membrane for volatile substances, such as room air fresheners, fragrances and other aromatic products, that satisfies the need for a permeable membrane which provides controlled release and increased permeation for a broad range of fragrances. The improved permeable membrane comprises a first permeable layer, a second permeable layer adhered to the first permeable layer, a third permeable sealant layer adhered to the second permeable layer and a release layer adhered to the first permeable layer opposite the second permeable layer. The first and third permeable layers include low density polyethylene and the second permeable layer comprises ultra low density polyethylene. The release layer includes a propylene copolymer and is adhered to the first permeable layer.

The release layer is selected from a material which will from only a weak heat bond with the first permeable layer, the adhesion of which is substantially less than the adhesion of the bond between the first permeable layer and the second permeable layer, as well as being less than the adhesion of the bond between the second permeable layer and the third permeable sealant layer to which it is adhered. The release layer can be easily pulled away from the permeable membrane layers by the user. As the release layer is pulled by the user to the area of the heat bond, the first permeable layer will split at the heat bond and remain bonded to the second permeable layer, while the release layer will part from the first permeable layer to allow the release layer to be peeled off. This leaves the permeable membrane layers exposed.

A preferred embodiment of the invention is used in a package tray which holds the fragrance formula. Because common volatile fragrances or perfumes are usually in liquid form at room temperature, an absorbent pad or gauge or paper is preferably used to carry the volatile liquid within the tray. The package comprises a thermoform. The third permeable layer of the permeable membrane is heat sealed to the thermoform tray to cover the tray. As above, the permeable membrane comprises a first permeable layer, a second permeable layer, and a third permeable layer. The first layer is adhered to the second layer and the second layer is adhered to the third layer. The first permeable layer of the permeable membrane is coextruded with the release layer to form a peelable bond between the layers. The package has a plurality of outer layers of material laminated together. The release layer with the coextruded permeable membrane is extrusion laminated to the outer layers. The outer layers of the laminate are selected to be impermeable to the liquid and its vapors, so that no vapors will escape as long as the package remains sealed.

Various materials such as metal foil may be used for the impermeable layer, and in such case it is desirable to protect the outer surface of the foil layers by adhering a tough protective layer thereto.

The package of this invention has the desirable feature of being relatively light and has no breakable parts which could be dangerous, while being very inexpensive to manufacture and thus suitable for dispensing small quantities of fragrances. As long as the package remains sealed, the volatile fragrance cannot escape, thus allowing very long shelf lives for the product. Special precautions during the handling of the product are unnecessary, since there are no parts that can be broken or easily damaged. Once the package has been opened by the consumer, the volatile vapors diffuse through the permeable layer at a controlled and selected rate. Because the process of transfer through the permeable layer is a diffusion process, rather than direct evaporation, the rate of release of vapor is relatively uniform over the expected life of the package.

In a preferred process for producing the package, the permeable membrane layers are cast extruded. The first permeable layer of the membrane is cast coextruded with the release layer to form a very uniform but weak bond between the two layers. This film is extrusion laminated onto one of the impermeable outer layers by using an adhesive which provides a long lasting and uniform bond between the two materials. The third permeable sealant layer is then heat sealed over a thermoformed tray containing a fragrance formula.

The process of heat bonding the layers of the package together is preferably accomplished by using a die having a lip or protrusion extending slightly beyond the face of the remainder of the die. When such a die is pressed onto the impermeable outer layers and against a resilient backing, the thermoplastic permeable membrane layers will soften and spread apart from the line of the protrusion on the die to form a line of weakness. This line of weakness is advantageous in allowing the first permeable layer to split easily as the package is peeled open by a user. To ensure the structural integrity of the package, it is preferable that the outer impermeable layers be formed of material which will not melt at the temperature of the bonding die.

For optimum performance of the package, it is also preferred that the line of weakness, and the wider heat bond adjacent to it, be formed in a V or a chevron shape at a position spaced away from one end of the package. The user easily peels open the package up to the point of the chevron, with the weakened first permeable layer splitting at the chevron to allow the remainder of the package to be peeled apart. The provision of the line of weakness can be dispensed with where the cohesive integrity of the first permeable layer will be split along the initial line of the bond.

These and other features, aspects and advantages of the patent invention will be apparent from the following detailed description appended claims and accompanying drawings showing preferred embodiments of the present invention.

BRIEF DESCRIPTION OF THE DRAWINGS

In the drawings:

FIG. 5 is a graph showing the weight of fragrance in grams lost as plotted against time for an air freshener utilizing a standard three layer, low density polyethylene film versus the multilayer film of the instant invention as defined in Example 1.

DESCRIPTION

Figure 1:
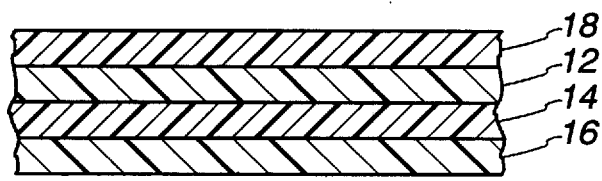
FIG. 1 is a cross-section of one embodiment of a multilayer membrane of this invention.

Referring to the drawings, an embodiment of the invention is shown generally in FIG. 1. The membrane comprises a first permeable layer 12, a second permeable layer 14 adhered to the first layer 12, a third permeable sealant layer 16 adhered to the second layer 14 and a release layer 18 adhered to the first layer 12. The permeable layers 12, 14 and 16 are of thermoplastic material, which is permeable to the vapors of a volatile substance.

Examples of materials which are satisfactory for forming the permeable layers 12, 14 and 16 include high, medium, and low density, polyethylene ultra low density polyethylene and ethylene vinyl acetate copolymer, as well as a number of other readily available polymer materials which are particularly adapted to use with a fragrance having an ethyl alcohol base. The degree of permeability of a particular polymer material can be increased by adding impurities such as calcium carbonate into the polymer material before the film membrane is formed in order to open up additional spaces between the polymer chains. Additional permeability may also be a by-product of coloring the layer by introducing solid micro particles of pigment, which also tends to open up spaces between the polymer chains.

The first permeable inner layer 12 is initially uniformly bonded to a release layer 18, which is composed of a material which does not form strong heat bonds with the first permeable layer 12 at the same temperatures at which bonds are formed between the two permeable layers 14 and 16. For example, polypropylene can be utilized as the release layer in conjunction with a polyethylene or ethylene vinyl acetate first permeable layer, in which case it is further desired to coextrude the permeable layer and release layer material together at a fairly low temperature to provide a very uniform but weak bond between the two film materials.

Figure 2:
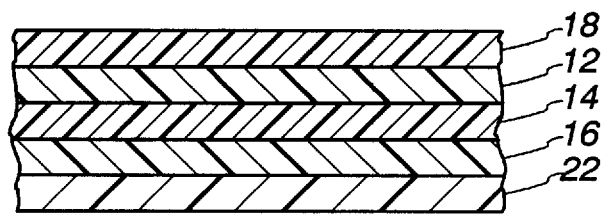
FIG. 2 is a cross-section of another embodiment of a multilayer membrane of this invention.

Another preferred embodiment of the invention is shown in FIG. 2. The membrane is shown in a five layer configuration. The membrane comprises a first permeable layer 12, a second permeable layer 14 adhered to the first layer 12, a third permeable layer 16 adhered to the second layer and a fourth permeable sealant layer 22 adhered to the third layer 16. A release layer 18 is adhered to the first permeable layer 12.

Examples of materials which are satisfactory for forming the permeable layers 12, 14, 16 and 22 include high, medium, and low density, polyethylene, very low density polyethylene and ethylene vinyl acetate copolymer, as well as a number of other readily available polymer materials, which are particularly adapted to use with a fragrance having an ethyl alcohol base. The degree of permeability of a particular polymer material can be increased by adding impurities such as calcium carbonate into the polymer material before the film is formed in order to open up additional spaces between the polymer chains. Additional permeability may also be a by-product of coloring the layer by introducing solid micro particles of pigment, which also tends to open up spaces between the polymer chains.

The first permeable layer 12 is initially uniformly bonded to a release layer 18 which is composed of a material which does not form strong heat bonds with the first permeable layer 12 at the same temperatures at which bonds are formed between the permeable layers 12, 14, 16 and 22. For example, copolymers of polypropylene and homopolymers of polypropylene can be utilized as the release layer in conjunction with a polyethylene or ethylene vinyl acetate first permeable layer, in which case it is further desired to coextrude the permeable layer and release layer material together at a fairly low temperature to provide a very uniform but weak bond between the two film materials.

Figure 3:
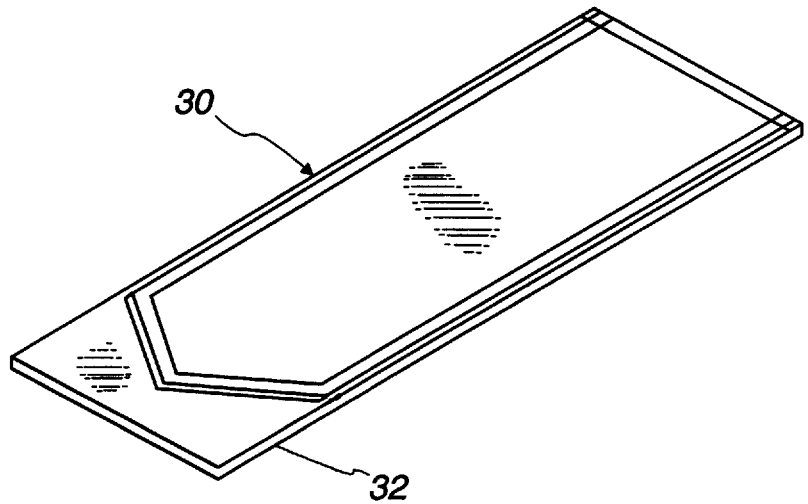
FIG. 3 is an exterior perspective view of a package in accordance with this invention.

Referring to the drawings, a preferred embodiment of the present invention is a package for selectively providing controlled release of vapors from a volatile substance is shown generally in an exterior view at 30 in FIG. 3. The package is shown in FIG. 3 in its unopened condition, in which the volatile fragrance or perfume is sealed within the package. The package is opened by a user by pulling apart the package at corners shown generally at 32.

Figure 4:
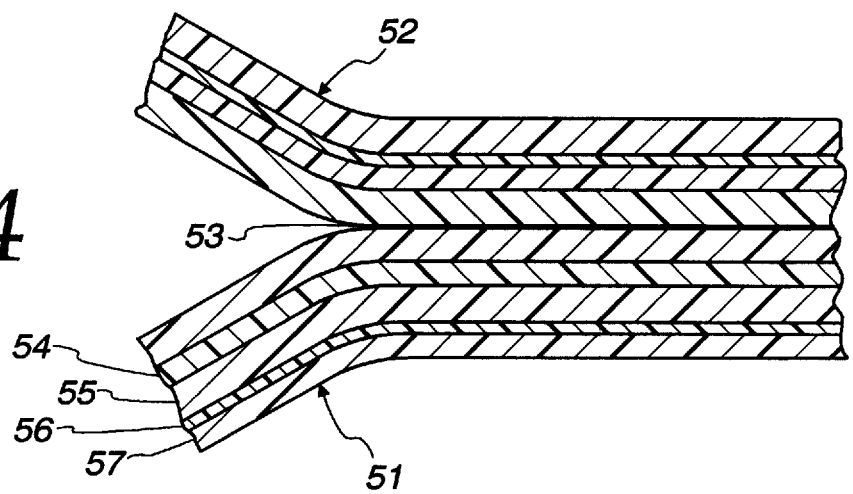
FIG. 4 is an expanded cross-sectional view of the package illustratively showing the bond formed by a heated rate.

The structure of the package is best shown with reference to the cross-sectional view of FIG. 4, which pictorially illustrates the plurality of layers and their relationship in making up the laminated package. As described further below, the package is formed in two parts, having a first laminated panel 51 and a cast extruded film 52 which meet together at a joint or interface 53, with the volatile substance (not shown in FIG. 4) being interposed between the first panel and the cast extruded film.

The outer layer 54 has the primary function of preventing the escape of any of the volatile vapors from the interior of the package during the shelf life of the package. Where a foil material such as aluminum foil is used (which may be in the range of 0.0005 inch in thickness), it is desirable to protect the foil layer with a tough outer layer of polymer material. In particular, the outer layer 54 may be coated with a laminant 55 similar to the laminant 56, and a protective layer 57 may be adhered thereto. The protective layer can be formed of Mylar polyester paper, cellophane, and various other polymer materials such as polypropylene.

The following examples are provided as illustrative of the invention, but should not be construed as being exhaustive or as limiting the invention to the specific details thereof.

EXAMPLE 1

The 3 layer permeable film for the multilayer membrane was produced on a cast line. The first permeable layer was formed from hot melting and cast extruding 12 lbs./ream low density polyethylene, Quantum NA-206. The second permeable layer was formed from hot melting and cast extruding 52 lbs./ream of a blend of 70% by weight ultra low density polyethylene, Union Carbide 9042 and 30% by weight low density polyethylene, Quantum NA-206. The third permeable layer was formed from hot melting and cast extruding low density polyethylene, Quantum NA-206.

The permeable film was cast coextruded with the release layer of 16 lbs./ream of a copolymer of propylene, Exxon PP-4663, at approximately 440° F. for the low density polyethylene in the first permeable layer and 485° F. for the propylene. The bond between the low density polyethylene in the first permeable layer and the propylene in the release layer was between 50–100 gm.

A seal was formed between the first permeable layer and the release layer by pressing the layers between a hot die and heated rubber backing on the bottom using a die temperature of approximately 485° F. applied for a sufficient period of time for the heat bonds to form (approximately 1 second). The third permeable layer was heat sealed to a thermoformed tray containing a fragrance formula.

Upon opening of the packages, by pulling the release layer apart from the first permeable layer, the first permeable layer of low density polyethylene split apart uniformly along the line of weakness in a V-shape and remained adhered to the second permeable inner layer. The fragrance could easily be detected, and a substantially constant fragrance level was observed for a period of approximately 50 days after opening.

The weight loss of the fragrance was compared to the weight loss of the fragrance using a standard film membrane as shown in FIG. 5. The standard membrane is comprised of three permeable layers of a low density polyethylene. The weight loss of the new film shows a quicker initial release of fragrance and more weight loss over time than the standard film.

EXAMPLE 2

A base material for the permeable layer was formed of 87% low density polyethylene resin 8% calcium carbonate an of 5% solid particulate pigment. The polyethylene blend was hot melted and coextruded at a temperature of 420° F. with polypropylene with the polyethylene layer having a 1½ mill thickness and the polypropylene layer having a ½ mill thickness. Two outer impermeable layers were formed by laminating 50 gauge Mylar polyester with 7 pounds per ream low density polyethylene laminant 0.0005 inch thickness aluminum foil 15 pounds per ream ethylene acrylic acid was extruded onto the bare side of one of the foil layers and polyethylene-polypropylene coextrusion was adhered onto the bare side of the other foil layer using 7 pounds per ream low density polyethylene as aluminant. A fragrance formula was sealed in a thermoform tray using the sealing die and method set forth in Example 1 above. The two panels of the package were pulled apart and the polyethylene permeable layer split along the v-shaped edge of the heat seal and delaminated from the polypropylene to leave only the permeable membrane covering the fragrance. Release of fragrance was detected for a period of approximately 7 days after opening.

EXAMPLE 3

A fragrance formula was heat sealed as described in Example 1 above.

EXAMPLE 4

A permeable film based mixture was formed of 85% ethylene vinyl acetate resin 10% calcium carbonate, and 5% particulate green pigment. This mixture was hot melted and coextruded with polypropylene as release layer to a thickness of ½ mil polypropylene and 1 mil ethylene vinyl acetate mixture.

Outer impermeable layers were formed by adhering 48 gauge Mylar polyester to 0.00035 inch foil using 7 pounds per ream low density polyethylene as an adhesive. On the bare aluminum foil side of one of the outer layers ethylene acrylic acid polymer was coated with a modified polypropylene prime available from Morton Chemical Company under the name Morphine to a thickness of 1 pound per ream after drying.

The polypropylene side of the laminated release film and permeable film adhered to the primed foil as prepared above using 10 pounds per ream polypropylene resin as an adhesive laminant.

It has been found that it is desirable to form a very uniform but weak bond between the release layer and the permeable layer to allow proper delamination between these layers when the packages is pulled apart. Preferably, the strength of these bonds will be in the range of 50 to 75 grams per inch, as tested on an Instron tester at 180° with a free tail at 10 inches per minute. The bond is preferably uniform to prevent the perfume and alcohol from seeping through the permeable layer and the release layer. Such pockets of perfume could produce unwanted excess discharge of perfume deodorizer when the package is initially opened. The case coextrusion process has been found to provide such a desirable bond between the common materials utilized for the two layers, such as polyethylene or ethylene vinyl acetate for the permeable layer and polypropylene for the release layer. For such a case, it is then found that it is most desirable to maintain the temperature of the hot melt of the mixture going into the coextruder at 400° F. 420° F. an opposed to the higher temperature normally used to provide coextrusions between these materials.

It is understood that the invention is not confined to the particular embodiments herein described as illustrative of the invention, but embraces all such modifications thereof as come with the scope of the following claims.

What is claimed is:

1. A membrane permeable to atmospheric diffusion of aromatic compounds, the membrane comprising:

(a) a first permeable layer comprising low density polyethylene;

(b) a second permeable layer adhered directly to one side of said first layer, comprising an ultra low density polyethylene, (c) a third permeable layer adhered to said second layer opposite said first layer, comprising a low density polyethylene; and (d) a release layer adhered directly to said first layer opposite said second layer, comprising polypropylene; wherein the bond strength between the release layer and the first layer is less than the bond strength between the first and second layers and the second and third layers, and wherein the release layer delaminates from the first permeable layer when a force is applied.

2. A package comprising the membrane of claim 1.

3. An extruded multilayer membrane permeable to atmospheric diffusion of aromatic compounds comprising:

(a) a first permeable layer comprising LDPE;

(b) a second permeable layer adhered to one side of said first layer, comprising a blend of ULDPE and LDPE;

(c) a third permeable layer adhered to said second layer opposite said first layer, comprising LDPE;

(d) a fourth permeable layer adhered to said third layer opposite said second layer, comprising a blend of ULDPE and LDPE; and (e) a release layer adhered to said first layer opposite said second layer, comprising polypropylene; wherein the bond strength between the release layer and the first layer is less than the bond strength between the first and second layers, the second and third layers and the third and fourth layers, and wherein the release layer delaminates from the first permeable layer when a force is applied.

4. A package comprising the membrane of claim 3.

5. A process for making a membrane permeable to atmospheric diffusion of aromatic compounds by cast extruding a first permeable layer comprising LDPE, a second permeable layer comprising ultra low density polyethylene, and a third permeable sealant layer comprising LDPE; coextruding a release layer comprising polypropylene with the first permeable layer to form a peelable bond wherein, the first layer is disposed between the second layer and the release layer and the third layer is adhered to the second layer opposite the first layer; wherein the bond strength between the release layer and the first layer is less than the bond strength between the first and second layers and the second and third layers, and wherein the release layer delaminates from the first permeable layer when a force is applied.

6. A process for making a membrane permeable to atmospheric diffusion of aromatic compounds by cast extruding a first permeable layer comprising LDPE, a second permeable layer comprising ultra low density polyethylene, and a third permeable layer comprising LDPE, and a fourth permeable sealant layer comprising ultra low density polyethylene; coextruding a release layer comprising polypropylene with the first permeable layer to form a peelable bond wherein, the first layer is disposed between the second layer and the release layer and the third layer is adhered to the second layer opposite the first layer; wherein the bond strength between the release layer and the first layer is less than the bond strength between the first and second layers and the second and third layers, and wherein the release layer delaminates from the first permeable layer when a force is applied.

* * * * *